US00PP35470P2

(12) United States Plant Patent
Dirr et al.

(10) Patent No.: US PP35,470 P2
(45) Date of Patent: Nov. 14, 2023

(54) ***ABELIA* PLANT NAMED 'ABLR-PII'**

(50) Latin Name: ***Abelia* x *grandiflora***
Varietal Denomination: ABLR-PII

(71) Applicant: Premier Introductions, Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/102,090

(22) Filed: Jan. 27, 2023

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
CPC ..... A01H 5/02; A01H 5/00; A01H 6/00
See application file for complete search history.

(56) References Cited

U.S. PATENT DOCUMENTS

PP15,203 P2 * 10/2004 Crowder ..... A01H 5/02
Plt./226

* cited by examiner

*Primary Examiner* — June Hwu
(74) *Attorney, Agent, or Firm* — Cassandra Bright

(57) ABSTRACT

A new and distinct cultivar of *Abelia* plant named 'ABLR-PII', characterized by its compact, mounding to spreading growth habit, with foliage color emerging red to pink, turning to a cream-white and green variegation. Semi-evergreen foliage does not photo bleach or burn in full sun like other variegated foliage cultivars. Plants maintain a spreading, layered growth habit without splaying shoots. The new variety is an *Abelia*, normally produced as an outdoor garden or container plant.

4 Drawing Sheets

Latin name of the genus and species: *Abelia* x *grandiflora*.
Variety denomination: 'ABLR-PII'.

BACKGROUND OF THE INVENTION

The present invention relates to a new and distinct cultivar of *Abelia* plant, botanically known as *Abelia* x *grandiflora*, commonly known as *Abelia*, and hereinafter referred to by the cultivar name 'ABLR-PII'. 'ABLR-PII' is grown primarily as an ornamental for landscape use.

'ABLR-PII' was discovered in 2020. The cultivar originated as a naturally occurring non-induced branch mutation, on an individual plant of the unpatented *Abelia* x *grandiflora* 'Little Richard', in a nursery in Watkinsville, GA. The branch sport was found on a containerized plant of the parent variety. The cultivar 'ABLR-PII' was initially selected by the inventors because of the variegated foliage. Later testing showed the new variety also has a favourable compact growth habit, and attractive flower characteristics. The cultivar is characterized by stable variegated green and white leaves with pink margins in the spring, fall, and anytime the weather is cooler. Plant habit is compact-spreading without the splaying shoots common to most *Abelia* cultivars.

Asexual reproduction of 'ABLR-PII' was first performed in 2020 by stem cuttings in Watkinsville, Georgia. Subsequent propagation since 2020 has shown that all the unique features of this new *Abelia*, as herein described, are stable and reproduced true-to-type through successive generations of such asexual propagation.

SUMMARY OF THE INVENTION

The cultivar 'ABLR-PII' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABLR-PII'. These characteristics in combination distinguish 'ABLR-PII' as a new and distinct *Abelia* cultivar:

1. Compact, mounding to spreading growth habit.
2. The foliage color emerges red to pink, turning to a cream-white and green variegation.
3. Semi-evergreen foliage that does not photo bleach or burn in full sun like some of the variegated foliage cultivars.
4. Light pink flower buds that open to white flowers with persistent pink sepals.
5. Maintains, a spreading, layered growth habit without splaying shoots.

PARENT COMPARISON

Plants of the new cultivar 'ABLR-PII' are similar to plants of the parent variety in most horticultural characteristics, however, plants of the new cultivar 'ABLR-PII' differ in the following:

1. Plants of 'ABLR-PII' have a dense compact habit, smaller size, and variegated foliage, whereas 'Little Richard' exhibits a larger more spreading growth habit and green foliage.

COMMERCIAL COMPARISON

Plants of the new cultivar 'ABLR-PII' can be compared to the variety *Abelia* 'Mardi Gras' U.S. Plant Pat. No. 15,203.

These varieties are similar in most horticultural characteristics however, 'ABLR-PII' differs in the following:

1. 'Mardi Gras' has a larger more open and upright plant, while 'ABLR-PII' is compact without the splaying shoots.

Plants of the new cultivar 'ABLR-PII' can be compared to the variety *Abelia* 'Bailbeliaone', U.S. Plant Pat. No. 33,071. These varieties are similar in most horticultural characteristics however, 'ABLR-PII' differs in the following:

1. The emerging spring foliage of 'Bailbeliaone' is 100% green, gradually developing the variegated trait. The emerging foliage color of 'ABLR-PII' is red to pink, turning to a cream-white and green variegation.
2. Leaves of 'Bailbeliaone' are distinctly smaller than 'ABLR-PII'.
3. 'Bailbeliaone' develops green reversion shoots while 'ABLR-PII' does not.

BRIEF DESCRIPTION OF THE PHOTOGRAPHS

The accompanying color photographs illustrate the flower and foliage characteristics and the overall appearance of 'ABLR-PII', showing the colors as true as it is reasonably possible to obtain in color reproductions of this type. Colors in the photographs may differ slightly from the color values cited in the detailed botanical description which accurately describe the colors of the new *Abelia*.

Figure 1:
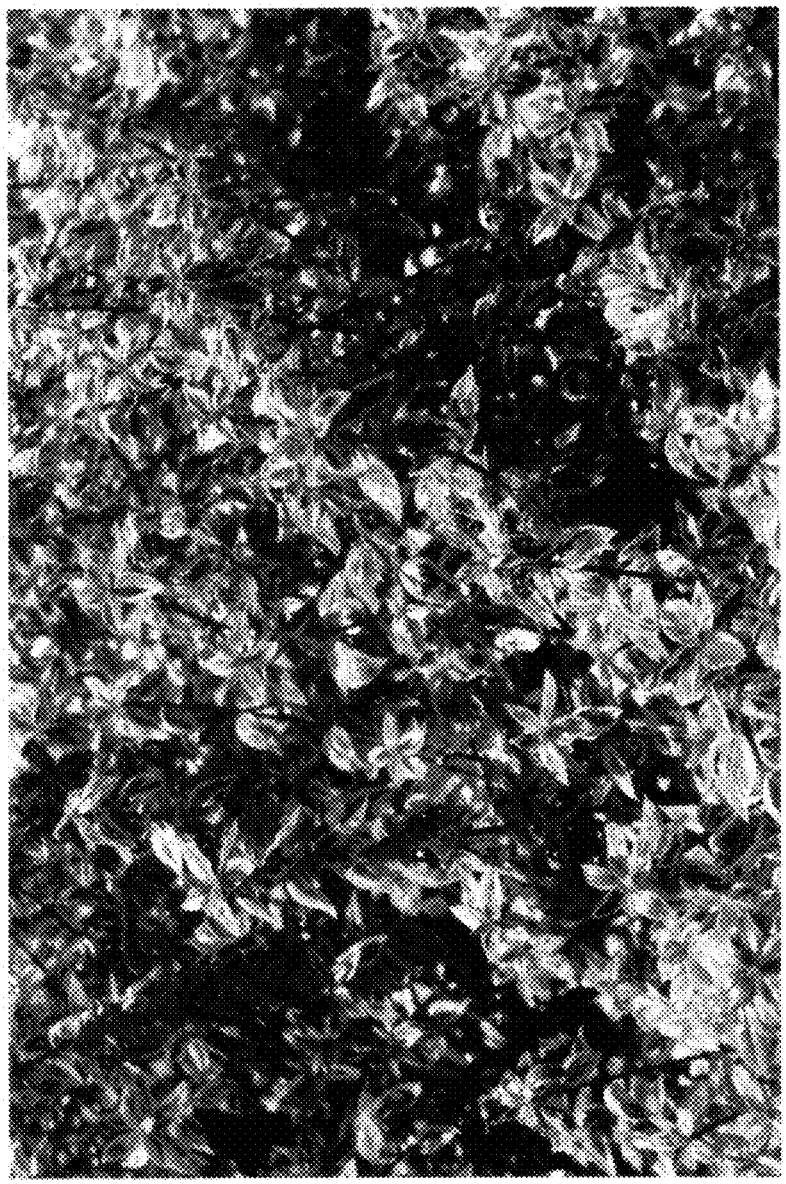
FIG. 1 illustrates the emerging foliage of 'ABLR-PII'.
Figure 2:
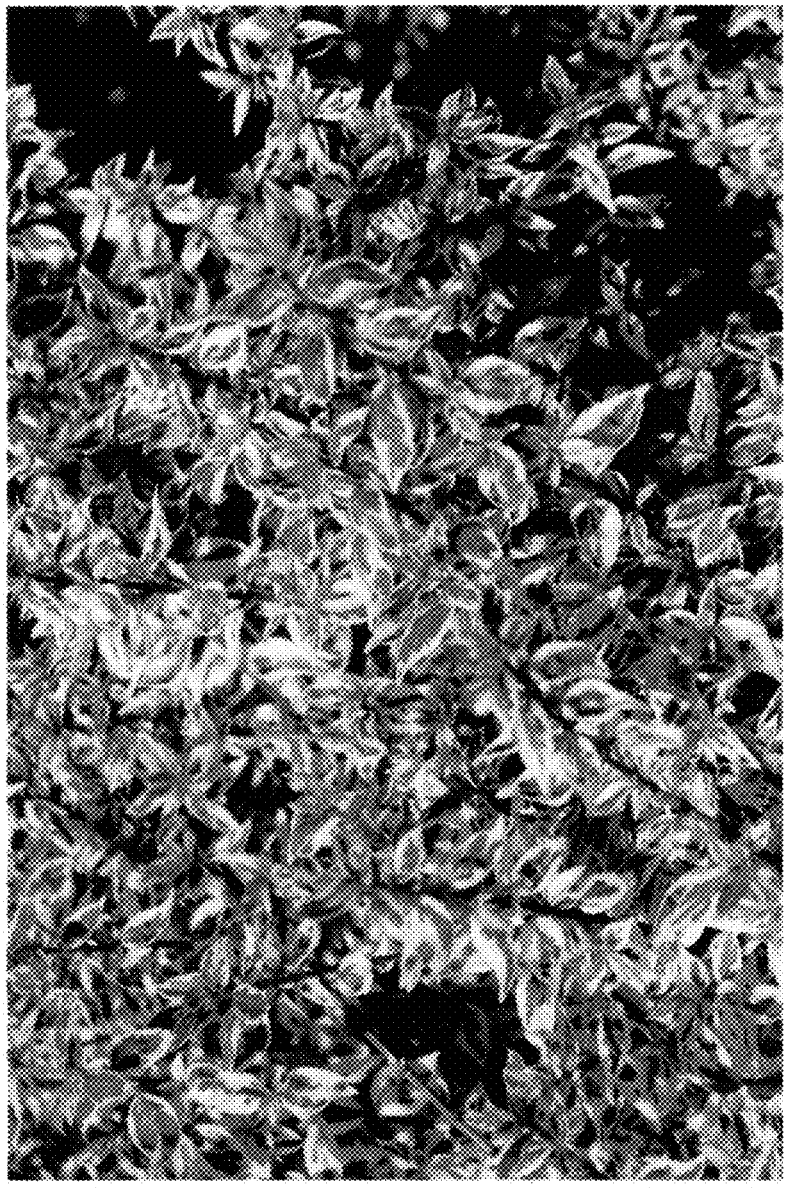
FIG. 2 illustrates typical foliage of 'ABLR-PII'.
Figure 3:
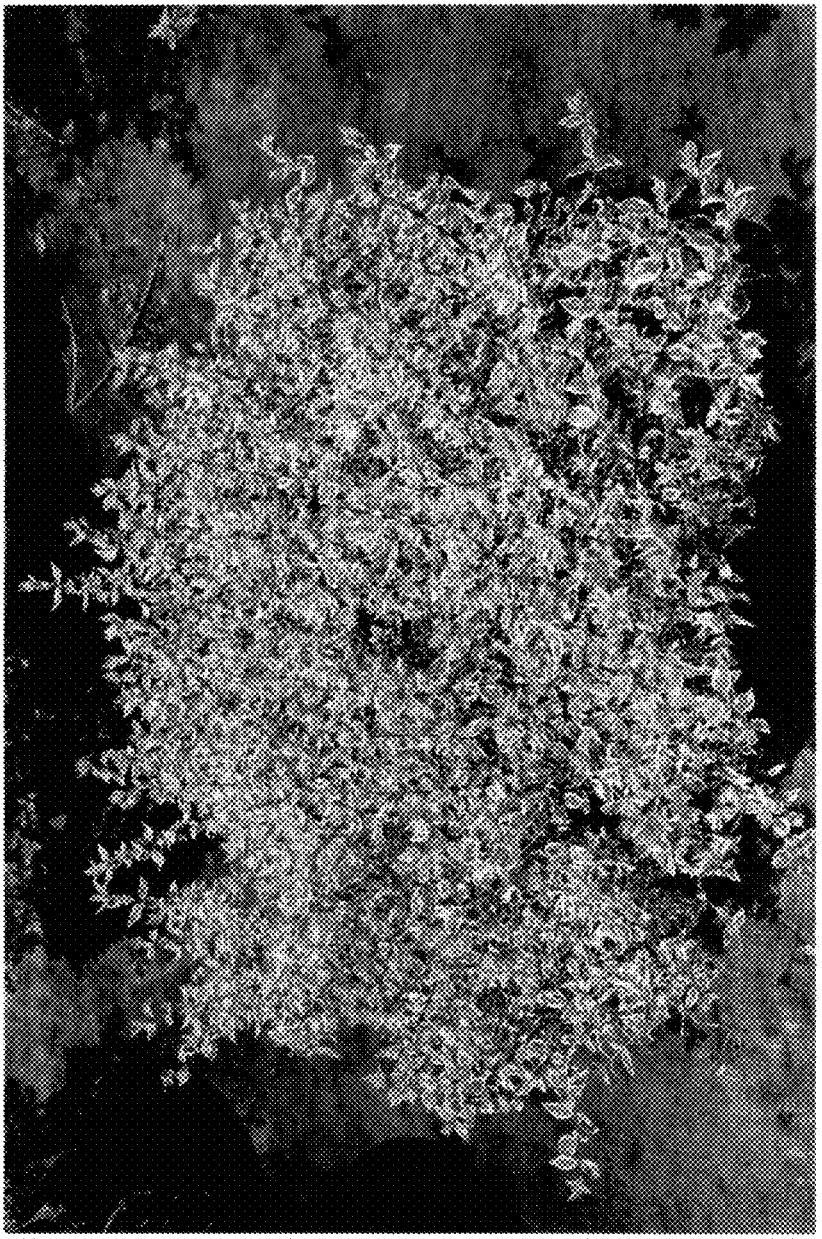
FIG. 3 illustrates the habit and overall appearance of a plant of 'ABLR-PII'.
Figure 4:
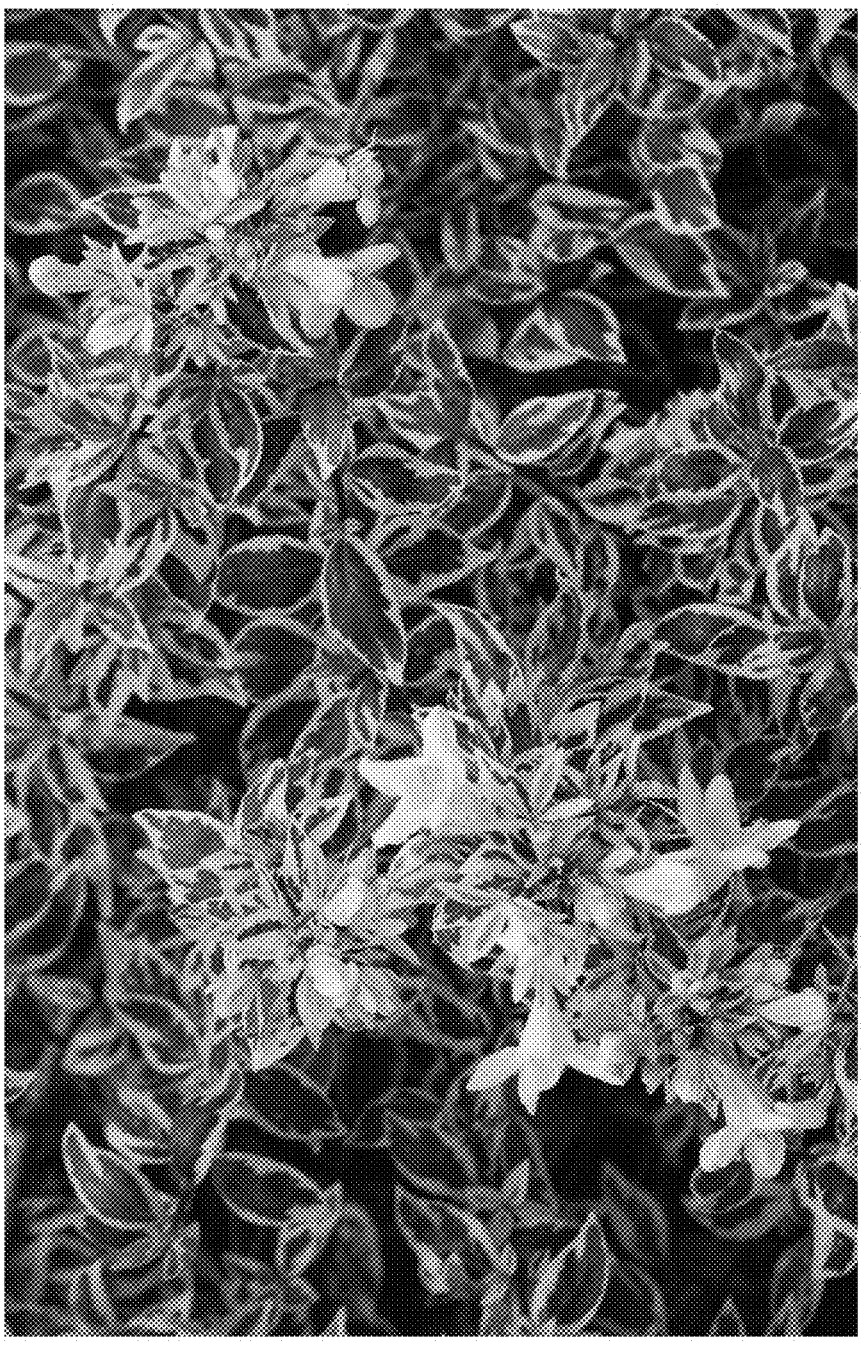

IG. 4 illustrates a close-up view of flowers.

DETAILED BOTANICAL DESCRIPTION

In the following description, color references are made to The Royal Horticultural Society Colour Chart, 2015 Edition, except where general terms of ordinary dictionary significance are used. Plants used for the description were approximately two-years-old and were grown in 23.03 L containers under outdoor conditions in Watkinsville, GA.

Botanical classification: *Abelia* x *grandiflora* 'ABLR-PII'.

PROPAGATION

Propagation: Terminal cuttings.

Time to initiate roots: About 21 days at 32° C. in the summer.

Time to produce a rooted young plant: About 40 days at 27° C. in summer.

Root description: Numerous, fine, fibrous and well-branched. Colored RHS White NN155C.

PLANT

Plant type: Small, semi-evergreen flowering shrub.

Age of plant described: Approximately 2 years.

Growth habit: Compact, mounding to spreading.

Pot size of plant described: 23.03 liter pot.

Overall plant shape: Rounded, spreading.

Height: 33 cm.

Plant spread: 86 cm.

Plant vigor: Moderate.

Growth rate: Moderate.

Branching characteristics: Freely branching; pruning enhances lateral branch development.

First-year stems:

*Diameter*.—2 mm.

*Shape*.—Round.

*Pubescence*.—Finely pubescent.

*Strength*.—Flexible.

*Color*.—Young: RHS Red 60A. Woody: RHS Grey-Yellow 197D.

Second-year stems:

*Diameter*.—3 mm or more.

*Shape*.—Terete.

*Strength*.—Easily broken.

*Color*.—RHS Grey-Yellow 197D.

Trunk/central stem:

*Diameter*.—1 cm at soil line.

*Color*.—RHS Greyed-Green 197D.

Internode length: About 1.1 cm.

Vegetative buds:

*Arrangement*.—Opposite. 2 pairs of bud scales.

*Length*.—About 1.5 mm.

*Width*.—About 1 mm.

*Shape*.—Ovoid.

*Pubescence*.—Finely pubescent.

*Color*.—RHS Greyed-Red 179B.

FOLIAGE

Leaf:

*Arrangement*.—Opposite, simple.

*Length*.—About 1.5 cm.

*Width*.—About 1 cm.

*Shape*.—Ovate.

*Apex*.—Acute.

*Base*.—Rounded.

*Margin*.—Crenate.

*Texture of top surface*.—Glabrous.

*Texture of bottom surface*.—Glabrous.

*Color*.—Developing Foliage, Upper Side: Center RHS Green 137B with Greyed-Purple 184D margins. Developing Foliage, Under Side: Center RHS Green 138B with Greyed-Purple 186C margins. Intermediate Foliage, Upper Side: Center RHS Green 137B with Greyed-Red 179D margins. Intermediate Foliage, Under Side: Center RHS Green 138C with Greyed-Red 179D margins. Mature Foliage, Upper Side: Center RHS Green 138B with Yellow 8D margins. Marginal coloration is about 10% 30% of leaf surface. Some spots of Green 138B within margin. Some leaves have irregular streaks or spots of 8D within the entire leaf blade. Mature Foliage, Under Side: Center RHS Green 138C with White 155D margins. Fall/Winter Foliage: Mixture of RHS Red-Purple 60B, Green 137B, and White 155A.

*Venation*.—Pattern: Pinnate. Color: Emerging Foliage, Upper Side: RHS White 155A. Emerging Foliage, Under Side: RHS Greyed-Green 193A. Intermediate Foliage, Upper Side: RHS Green-Yellow 1C. Intermediate Foliage, Under Side: RHS Green-Yellow 1D. Mature Foliage, Upper Side: RHS Yellow-Green 146C. Mature Foliage, Under Side: RHS Yellow-Green 147D.

*Petiole*.—Length: About 3 mm. Diameter: About 1 mm. Color, Upper Side: RHS Red-Purple 58A. Color, Under Side: RHS Red-Purple 58A. Pubescence: Finely pubescent.

FLOWER

Natural flowering season: May to June, sporadically until frost in Watkinsville, GA.
General quantity of flowers per plant: Few.
Inflorescence:
*Type*.—Terminal and axillary panicles containing campanulate flowers.
*Height*.—3.5 cm.
*Width*.—4.5 cm.
*Flowers and buds per inflorescence*.—Average range 10 to 20 flowers and buds.
Individual flowers:
*Depth*.—2 cm.
*Diameter*.—1 cm.
*Persistence*.—Persistent.
*Fragrance*.—Faint, pleasant.
Bud:
*Shape*.—Spatulate.
*Length*.—2.2 mm.
*Diameter*.—4 mm.
*Color*.—RHS White N155B.
Petal:
*Number*.—5.
*Shape*.—Roughly spatulate.
*Margin*.—Entire.
*Apex*.—Obtuse.
*Lobe length*.—5 mm.
*Lobe width*.—4 mm.
*Corolla lobe attitude*.—Upright.
*Corolla tube length*.—1 cm.
*Texture*.—Upper: Smooth, with fine, sparse pubescence. Lower: Smooth, with fine, sparse pubescence.
*Color*.—Upper Surface: RHS White NN155B. Lower Surface: RHS White NN155B.
*Tube color*.—Interior White N155C, exterior N155B.
Pedicel:
*Length*.—5 mm.
*Texture*.—Finely pubescent.
*Color*.—RHS Greyed-Red 182A.
Calyx:
*Arrangement*.—Single whorl of 5 sepals.
*Length*.—8 mm.
*Diameter*.—3 mm.
*Base*.—Fused.
*Color*.—RHS Red 52D.
*Pubescence*.—None.

REPRODUCTIVE ORGANS

Stamens:
*Number*.—5.
*Length*.—5 mm.
*Width*.—Less than 0.5 mm.
*Filament length*.—4 mm.
*Filament width*.—0.5 mm.
*Filament color*.—RHS White N155B.
Anthers:
*Shape*.—Linear.
*Length*.—2.5 mm.
*Width*.—1 mm.
*Color*.—RHS White N155A.
*Pollen color*.—RHS White N155A.
*Pollen amount*.—Small quantity.
Pistil:
*Number*.—1.
*Length*.—2.5 cm.
*Diameter*.—Less than 0.5 mm.
*Style*.—Length: 1.7 cm. Width: 1 mm. Color: RHS White N155D.
*Stigma*.—Shape: Round. Length: 1 mm. Color: RHS White 155B.
*Ovary*.—Number: 1 inferior ovary per flower. Length: 7 mm. Width: 1 mm. Color: RHS Greyed-Orange 173B.

FRUIT

Type/appearance: One-seeded, leathery, tubular achene.
Length: About 6 mm.
Width: About 2 mm.
Mature color: RHS Green 143C.

OTHER CHARACTERISTICS

Disease/pest resistance: Neither resistance nor susceptibility to normal diseases and pests of *Abelia* x *grandiflora* have been observed.
Temperature tolerance: USDA Plant Hardiness Zone Map (2012) Zone 6 to 9.

What is claimed is:

1. A new and distinct cultivar of *Abelia* plant named 'ABLR-PII' as herein illustrated and described.

* * * * *